United States Patent [19]

Millauer et al.

[11] Patent Number: 4,460,512
[45] Date of Patent: Jul. 17, 1984

[54] ω-FLUOROSULFATO-PERFLUOROCARBOXYLIC ACID DERIVATIVES AND PROCESSES FOR THEIR PREPARATION

[75] Inventors: Hans Millauer, Eschborn; Werner Schwertfeger, Butzbach, both of Fed. Rep. of Germany

[73] Assignee: Hoechst Aktiengesellschaft, Frankfurt am Main, Fed. Rep. of Germany

[21] Appl. No.: 482,570

[22] Filed: Apr. 6, 1983

Related U.S. Application Data

[62] Division of Ser. No. 300,945, Sep. 10, 1981, abandoned.

[30] Foreign Application Priority Data

Sep. 12, 1980 [DE] Fed. Rep. of Germany ....... 3034538

[51] Int. Cl.³ ............................................ C07C 141/00
[52] U.S. Cl. ................................. 260/458 F; 560/180; 204/59 F; 204/72; 204/79
[58] Field of Search ......................... 260/456 F, 458 F

[56] References Cited

PUBLICATIONS

Lustig et al., Inorg. Chem., 3, 287 (1964).

Primary Examiner—Nicky Chan
Attorney, Agent, or Firm—Curtis, Morris & Safford

[57] ABSTRACT

The present invention relates to novel ω-fluorosulfato-perfluorocarboxylic acid derivatives of the formula I

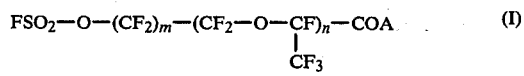

in which A denotes halogen, preferably Cl or F, and in particular F, or the group OR wherein R is alkyl, aryl or aralkyl with preferably up to 10 C atoms, in particular $CH_3$ or $C_2H_5$, m denotes a number from 1 to 10, preferably from 1 to 8 and in particular from 1 to 6, and n denotes a number from 0 to 10, preferably from 0 to 4 and in particular 0 or 1, which are prepared by electrolysis of ω-H-perfluorocarboxylic acid halides of the formula II

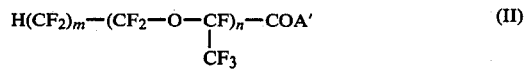

in which A'=halogen and m and n have the same meaning as in formula I, in an electrolyte consisting of fluorosulfonic acid/alkali metal fluorosulfonate, the compounds of the formula III being formed:

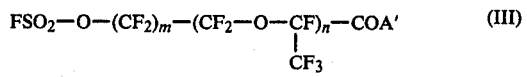

in which A' has the same meaning as in formula II and m and n have the same meaning as in formulae I and II, these compounds then also being esterified with an organic hydroxy compound of the formula IV

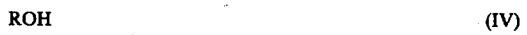

in which R has the meaning given in the case of formula I, to give compounds I in which A=OR.

The compounds of the present invention are valuable intermediate products particularly suitable for the preparation of perfluorinated vinyl compounds with an additional functional group wherein the vinyl compounds can in turn be processed to valuable oligomers and polymers which are very stable to heat and chemicals and can be used in many ways.

10 Claims, No Drawings

ω-FLUOROSULFATO-PERFLUOROCARBOXYLIC ACID DERIVATIVES AND PROCESSES FOR THEIR PREPARATION

This is a division, of application Ser. No. 300,945 filed Sept. 10, 1981 now abandoned.

Perfluorinated organic compounds are precursors, intermediates and end products for various specialized fields. Oligomeric perfluorinated vinyl compounds are, for example, valuable lubricating oils and antifriction substances with an exceptionally high resistance to chemicals and heat; higher-molecular (polymeric) compounds of this type are of importance as chemically stable and heat-stable coating and sealing materials, elastomers, if basic or acid groups are also present, and ion exchangers, for example for electrolysis cell membranes, and the like.

Perfluorinated monomeric vinyl compounds for such intended uses are known, for example, from U.S. Pat. No. 3,282,875. The compounds described in this Specification have the formula:

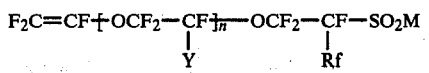

in which Rf=F or ($C_1$-$C_{10}$)-perfluoroalkyl, Y=F or $CF_3$, n=an integer from 1 to 3 and M=F, OH, amino or OMe (Me=an alkali metal or a quaternary ammonium group).

The compounds in which M=fluorine can be prepared by pyrolysis (at 200° to 600° C.) of the following compounds

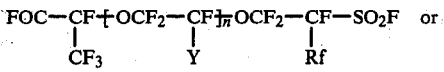

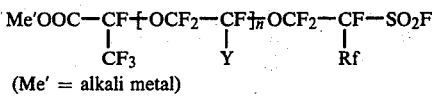

(Me' = alkali metal)

The following reaction takes place during pyrolysis:

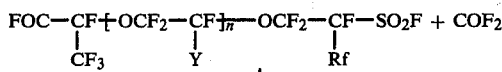

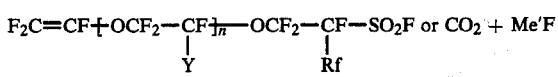

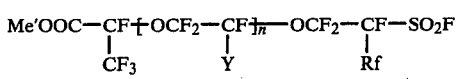

The compounds used for the pyrolysis are the subject of U.S. Pat. No. 3,301,893 and are prepared from perfluorinated fluorosulfonyl-carboxylic acid fluorides and perfluoroethylene oxide (or its derivatives), which may be illustrated with the aid of the following concrete example:

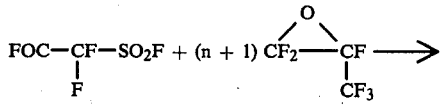

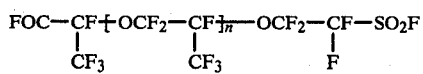

However, this process has the disadvantage that the perfluorinated fluorosulfonyl-carboxylic acid fluorides used as the starting materials can be prepared virtually only via sultones, during the production of which explosive mixtures ay be formed (Chem.Eng.News 49, Volume 22, page 3 (1971)). For example, the preparation of perfluorinated fluorosulfonylacetic acid is based on the following reaction:

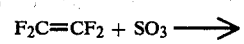

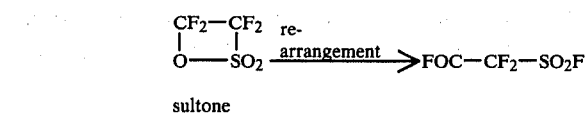

Mixtures of $SO_3$ and the sultone are unstable because of the following possible reaction:

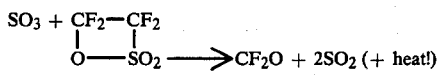

Other perfluorinated vinyl ethers are known from German Offenlegungsschrift No. 2,708,677. The compounds have the formula

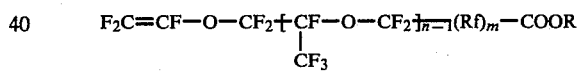

in which Rf=a bifunctional ($C_1$-$C_{10}$)-perfluoro group, R=alkyl, m=0 or 1 and n=a number from 1 to 5.

These compounds are prepared by pyrolysis of the following compounds

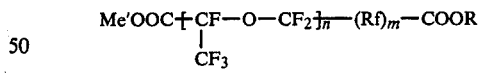

which are in turn obtained by reaction of the corresponding acid fluorides:

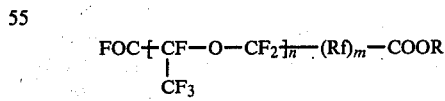

with an alkali metal carbonate (for example $Na_2CO_3$).

Some of the starting compounds for this pyrolysis can be obtained by the process described in German Offenlegungsschrift No. 2,751,050:

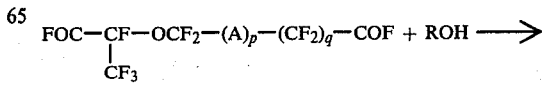

-continued

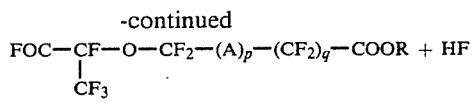

In the formulae, A=a bifunctional $(C_1-C_{10})$-perfluoro group, optionally with ether bonds (for example the

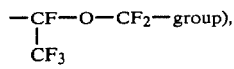

R=alkyl, p=0 or 1 and q=a number from 1 to 8.

However, this process does not proceed uniformly to give the desired compounds, but leads to mixtures of three derivatives. The isomeric half-esters and diesters which can be separated off only with difficulty and which together can amount to about 30% of the product cannot be used for the further synthesis to give the perfluorinated vinyl ethers.

Virtually the same compounds are also disclosed in German Offenlegungsschrift No. 2,817,366, and the formula given in that Specification is:

$$FOC{+}CF(CF_3){-}O{-}CF_2{\}_n{-}CF_2{-}COOR$$

in which R=$(C_1-C_6)$-alkyl and n=a number from 0 to 6.

The compounds are prepared as follows:
in which n=0:

$$R^1O-CF_2-CF_2-COOR + SO_3 \longrightarrow$$

$$(R^1 = C_1-C_6-\text{alkyl})$$

$$FOC-CF_2-COOR + R^1OSO_2F$$

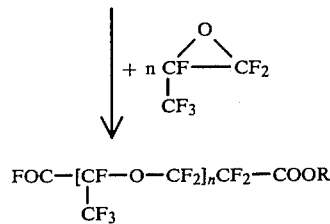

$$FOC-[CF(CF_3)-O-CF_2]_nCF_2-COOR$$

in which n=a number from 1 to 6:

The process is of practical importance only in the case of the starting compound $CH_3O-CF_2-CF_2-COOCH_3$. The by-product $CH_3-O-SO_2F$ formed therefrom in a stoichiometric amount in the reaction with $SO_3$ is a highly toxic compound which is as dangerous as dimethyl sulfate and similar methylating agents (Chem.Eng. News 56, Volume 37, page 56 (1978)).

In addition to the abovementioned perfluorinated sulfonyl fluorides containing the grouping

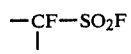

perfluorinated fluorosulfato compounds containing the structural unit

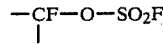

have also been disclosed. Such perfluorinated fluorosulfato compounds can be prepared, for example, by anodic oxidation of 1-H-perfluoroalkanes in a mixture of fluorosulfonic acid and an alkali metal fluorosulfonate using platinum electrodes (J.C.S.Chem.Comm. 1978, 118): for exampel

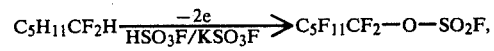

which probably proceeds via the intermediately formed peroxydisulfuryl difluoride $FSO_2-O-O-SO_2F$.

Such flurosulfato compounds can react, for example, with alcohols in the course of several days as follows:

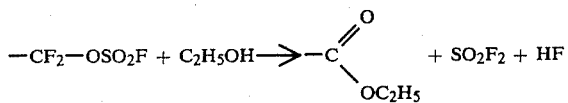

compare I zv. Akad.Nuak. SSSR, Ser. Khim.1974, English edition pages 441/42.

However, the perfluorinated fluorosulfato compounds have not yet achieved particular importance.

Because of the considerable importance of perfluorinated organic products and because the known processes, in particular those for the preparation of perfluorinated vinyl ethers which also have a further functional group, frequently present safety problems or are accompanied by side reactions which reduce the yield, there was the object of opening up a simpler and improved route to such compunds which does not proceed via explosive intermediates, leads uniformly to only the desired products and also gives no toxic by-products.

According to the invention, this object could be achieved by providing new bifunctional perfluoro compounds, that is to say ω-fluorosulfato-perfluorocarboxylic acid derivatives of the formula I:

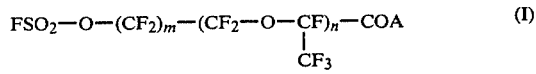

in which A denotes halogen, preferably Cl or F, and in particular F, or the group OR (R=alkyl, aryl or aralkyl with preferably up to 10 C atoms, in particular $CH_3$ or $C_2H_5$), m denotes a number from 1 to 10, preferably from 1 to 8 and in particular from 1 to 6, and n denotes a number from 0 to 10, preferably from 0 to 4 and in particular 0 or 1.

If A=halogen, the compounds are ω-fluorosulfato-perfluorocarboxylic acid halides, and if A=OR, the compounds are ω-fluorosulfato-perfluorocarboxylic acid esters.

Starting from the esters of the formula I (that is to say in which A=OR), corresponding bifunctional vinyl ethers are obtained by decomposition in the presence of an alkali metal fluoride by the process of U.S. Ser. No. 300,920, now U.S. Pat. No. 4,401,829 filed on the same day, and reaction of the product with hexafluoropropene oxide and subsequent splitting off of $COF_2$ in a known manner:

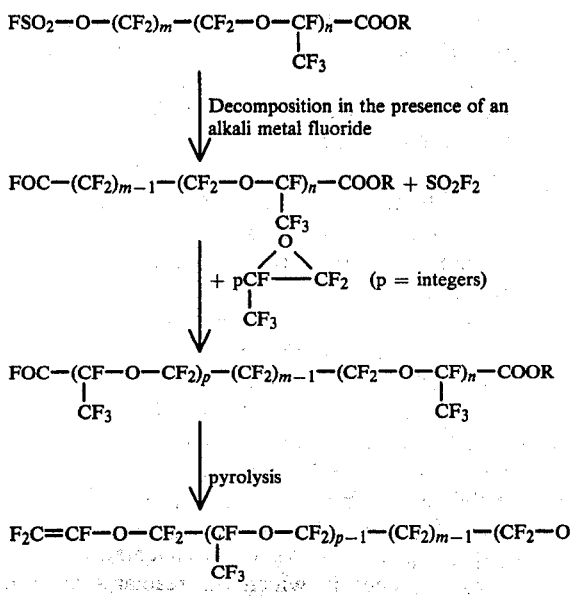

According to the invention, the compounds of the formula I are prepared by (a) electrolyzing ω-H-perfluorocarboxylic acid halides of the formula II

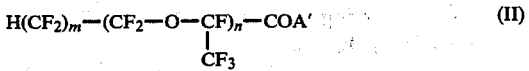

in which A′=halogen and m and n have the same meaning as in formula I, in an electrolyte comprising fluorosulfonic acid and an alkali metal fluorosulfonate, using anodes made of metals of the platinum group (osmium, iridium or platinum) and/or glassy carbon, and cathodes made of a customary material which is stable under the electrolysis conditions, isolating the ω-fluorosulfato-perfluorocarboxylic acid halides thereby formed, of the formula III

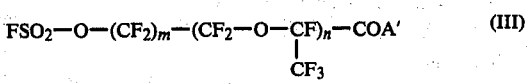

in which A′ has the same meaning as in formula II and m and n have the same meaning as in formulae I and II, and (b) esterifying these compounds with an organic hydroxy compound of the formula IV

in which R has the meaning given in the case of formula I, to give ω-fluorosulfato-perfluorocarboxylic acid esters of the formula I in which A=OR.

It was surprising that the two process stages (a) and (b) take place virtually without complications, because (a) the acid halide group of the ω-H-perfluorocarboxylic acid halides of the formula II is not attacked during the electrolysis and is thus unchanged, and because (b) no reaction of the fluorosulfato group takes place in the esterification stage; the latter was hardly to be expected, expecially in view of the reaction known from Izv. Akad. Nauk. SSSR, Ser. Khim. 1974, English edition, pages 441/42, in which perfluorinated ω-fluorosulfato compounds are reacted with alcohol to give the corresponding esters.

The starting compounds for the process according to the invention—that is to say the ω-H-perfluorocarboxylic acid halides of the formula II—can be obtained, for example, by the following known procedures:

1. J.Am.Chem. Soc. 74 (1952), 1426:

The following triazine derivative is first prepared from ammonia and tetrafluoroethylene in the presence of copper acetate:

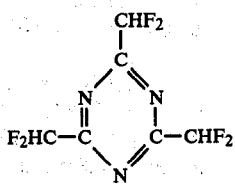

and is then converted into the sodium salt of difluoroacetic acid, $HCF_2$—COONa, by being heated with aqueous sodium hydroxide solution. The acid halides of the formula II (in which m=1 and n=0) can be obtained from this compound by known methods.

2. U.S. Pat. No. 2,559,629:

Aliphatic polyfluorocarboxylic acids and their salts are prepared by oxidation of polyfluoroalkanols with permanganate:

X=Cl or F, at least half the radicals X being F, and n=a number from 1 to 3.

The starting compounds for this oxidation are prepared from ethylene derivatives $CX_2=CX_2$ and methanol.

The acid halides are obtained from the resulting free acids in a known manner; the compounds in which all the radicals X=F are the compounds of the formula II in which m=an even number and n=0.

3. J. Org. Chem. Volume 42 No. 25 (1977), 4055:

This reference describes, inter alia, the following reaction:

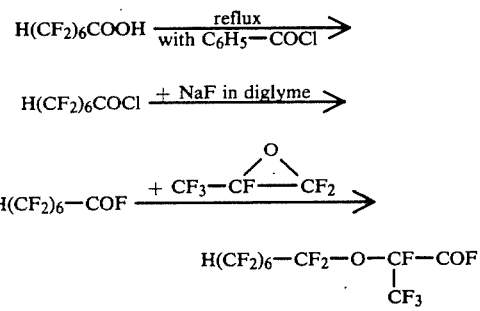

$$H(CF_2)_6CH_2OH \xrightarrow{\text{oxidation}}$$

$$H(CF_2)_6COOH \xrightarrow[\text{with } C_6H_5-COCl]{\text{reflux}}$$

$$H(CF_2)_6COCl \xrightarrow{+ \text{ NaF in diglyme}}$$

$$H(CF_2)_6-COF \xrightarrow{+ CF_3-CF\overset{O}{\underset{}{\diagdown}}CF_2}$$

$$H(CF_2)_6-CF_2-O-\underset{CF_3}{CF}-COF$$

The last three compounds of this reaction series are all compounds of the formula II; the other compounds falling within the formula II can also be obtained in a completely analogous manner.

The electrolysis stage (a) of the process according to the invention is in principle carried out in the manner known, for example, from J.CS.Chem.Comm.1978, 118.

The base electrolyte is most simply prepared by dissolving a readily accessible alkali metal chloride, for example LiCl, NaCl or KCl, in fluorosulfonic acid $FSO_3H$, which, if necessary, has first been subjected to purification by distillation, the hydrogen chloride liberated escaping from the solution or being driven out by introduction of a dry stream of nitrogen. The concentration of the alkali metal sulfonate in the electrolyte is not critical, and can be in the range from about 0.05 to about 3 moles per liter.

The starting substances of the formula II are dissolved or dispersed in the base electrolyte, it being possible to employ up to about 60% by weight of II, relative to the base electrolyte.

Suitable anode materials for the electrolysis are platinum or metals of the platinum group (Os, Ir or Pt) as well as platinum alloys containing up to about 90% by weight of other noble metals, in particular iridium, and/or glassy carbon. The material mentioned last is the preferred anode material, since it is particularly corrosion-resistant under the electrolysis conditions.

The cathode material is not critical for the process. In principle, therefore, all the possible known cathode materials can be used provided only that these are fairly stable under the electrolysis conditions prevailing here. Examples of suitable materials are platinum, copper, high-grade steel and glassy carbon.

The ratio of anode area to cathode area is generally between about 1:1 and about 10:1, and preferably about 5:1 to about 10:1.

In other respects, the electrolysis is most simply carried out in an undivided cell, it also being possible to use standard, laboratory breaker cells.

The current densities used are advantageously between about 10 and 150 $mA \times cm^{-2}$, preferably between about 20 and 80 $mA \times cm^{-2}$, and the electrolysis temperatures are between about 0° and 100° C., preferably between about 20° and about 40° C.

When the electrolysis has ended, the reaction product is separated off from the electrolysis mixture either by distillation, or in some cases also by decanting; the electrolyte phase which remains can be re-used for a subsequent batch, after being replenished with fresh fluorosulfonic acid.

The ω-fluorosulfato-perfluorocarboxylic acid halides of the formula III thus obtained can be further purified by fractional distillation. In some cases, fluorosulfonic acid can be removed completely by distillation only with difficulty. Fluorosulfonic acid-free ω-fluorosulfato-perfluorocarboxylic acid halides III can then be obtained, for example, by treatment of the crude product with NaF (if A'=F) and subsequent gentle distillation. However, small amounts of fluorosulfonic acid generally do not interfere in the subsequent esterification stage b.

Esterification with an organic hydroxy compound—in particular with methanol or ehtanol—is in principle carried out in a known manner in the presence or absence of an inert solvent, such as, for example, methylene chloride. The ω-fluorosulfato-perfluorocarboxylic acid halide III and the hydroxy compound IV are advantageously employed in a molar ratio of about 1:1 to about 1:1.5. A larger excess of the hydroxy compound is possible, but is of no particular advantage.

The sequence in which the reactants are brought together is also practically of no importance for the esterification. Preferably, however, the halide III is initially introduced in an inert solvent, and a solution of the hydroxy compound III in the same solvent or diluent is added, with cooling. It should in all cases be ensured that stirring is as thorough as possible, for uniform mixing of the batch.

The internal temperature of the batch is advantageously kept between about −80° and +70° C., preferably between about −20° and +40° C. and in particular between about 0° and +20° C., during the reaction.

Since hydrofluoric acid, which attacks borosilicate glass, is formed during the esterification if A'=F, it is advantageous, in this case, to carry out the reaction in a vessel made of material which is resistant to hydrofluoric acid.

When the reaction has ended, the hydrogen halide acid formed is removed, for example by washing the mixture with water, and the organic phase is dried and distilled.

The end products of the process according to the invention (esters of the formula I in which A=OR) are usually colorless liquids which are highly stable in the pure state.

The new compounds of the formula I according to the invention open up a new, simplified route to perfluorinated vinyl ethers which have a further functional group and are known per se, it being possible for these ethers to be processed in a known manner to give valuable chemically stable and heat-stable lubricants and anti-friction agents, coating and sealing materials, elastomers, ion exchangers and the like.

The advantage of the new route to perfluorinated vinyl ethers known per se which is made possible by the compounds I according to the invention, compared with the known routes, will become evident from the following comparison; the route from the common simple base products to the perfluorinated vinyl ethers has not been shown in entirety, but only as far as the vinyl ether precursors (perfluorinated dicarboxylic acid fluoride-esters) common to all the routes.

COMPARISON A: PREPARATION OF FOC—CF₂—COOCH₃

1. Via the compound of the formula I according to the invention, in which m=2, n=0 and A=CH₃ (=FSO₂—O—CF₂—CF₂—COOCH₃):

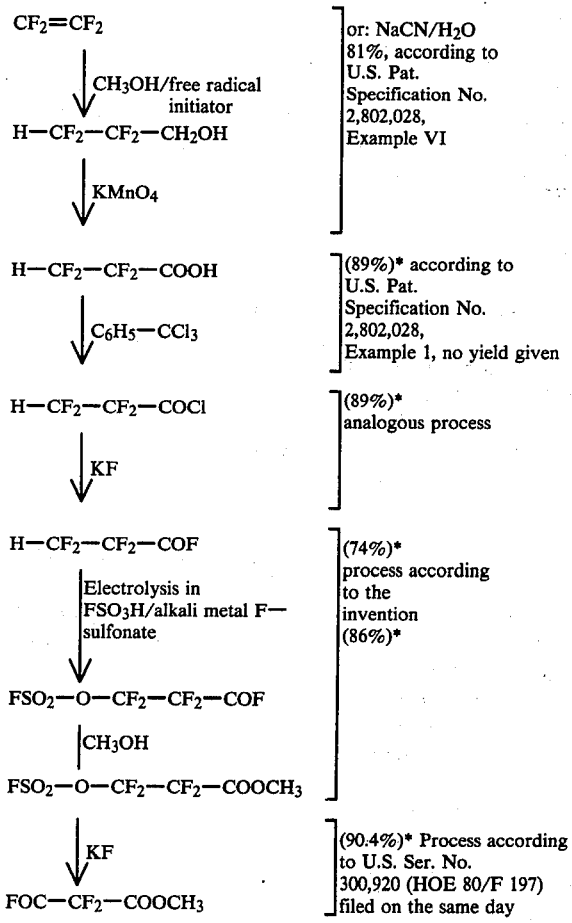

2. According to the state of the art (DuPont):

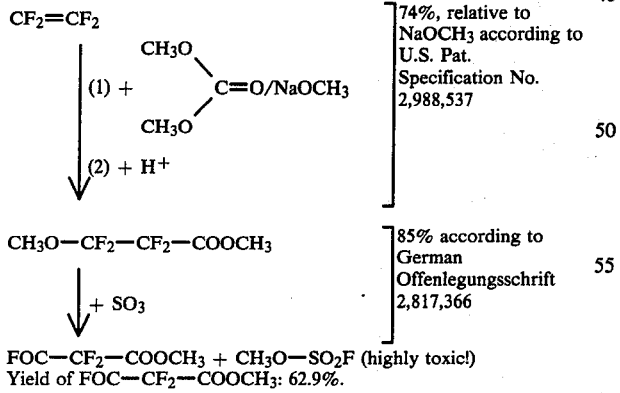

The following statements are to be taken into consideration:

(a) The amount of CF₂=CF₂ employed was not determined, so that the yield relative to CF₂=CF₂ cannot be given. In addition, a by-product is formed in this reaction in a yield of at least 12%.

(b) The yield of FOC—CF₂—COOCH₃ in the second stage is determined from the mixture of FOC—CF₂—COOCH₃/CH₃—O—SO₂F by gas chromatography. The fluorosulfonic acid methyl ester, which is highly toxic, is separated off by passing the mixture over NaF at about 400° C., this separation also being incomplete. No further yield is given for the purified FOC—CF₂—COOCH₃.

In spite of the fact that this route according to the state of the art appears relatively simple, it is, however, less advantageous than the route made possible by the invention, in particular because of the unavoidable formation of the highly toxic CH₃OSO₂F.

COMPARISON B: PREPARATION OF FOC—CF₂—CF₂—CF₂—COOCH₃

1. Via the compound of the formula I according to the invention in which m=4, n=0 and A=CH₃ (=FSO₂—O—CF₂—CF₂—CF₂—CF₂—COOCH₃):

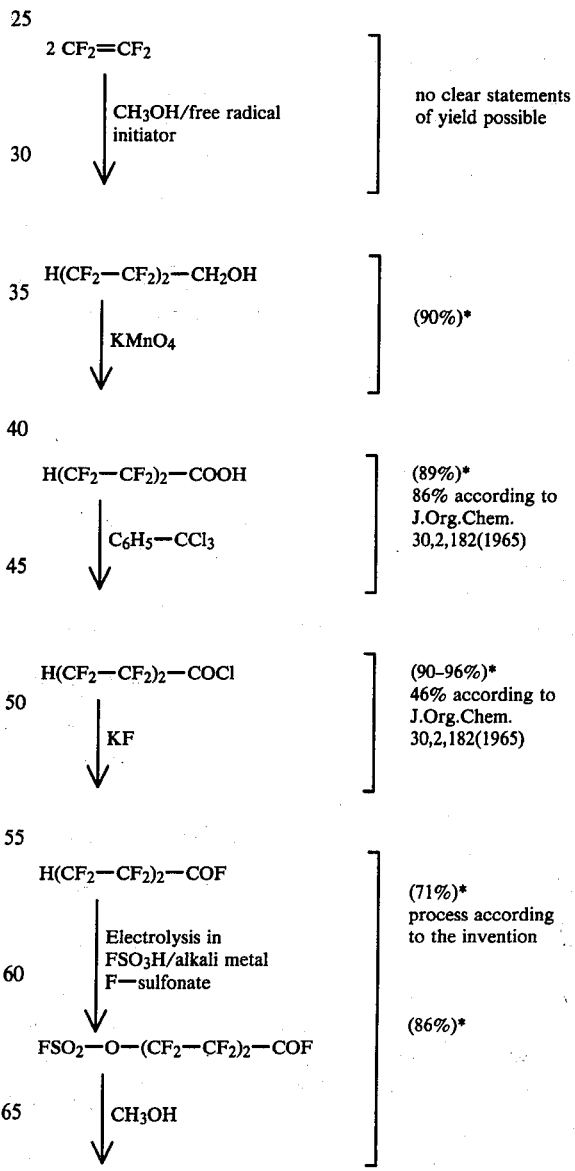

-continued

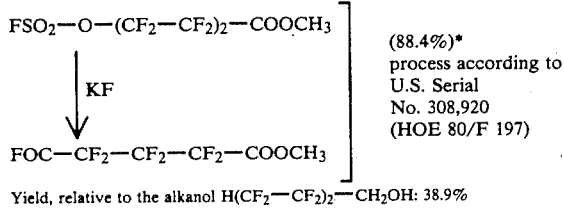

(88.4%)* process according to U.S. Serial No. 308,920 (HOE 80/F 197)

Yield, relative to the alkanol H(CF₂—CF₂)₂—CH₂OH: 38.9%

2. According to the state of the art

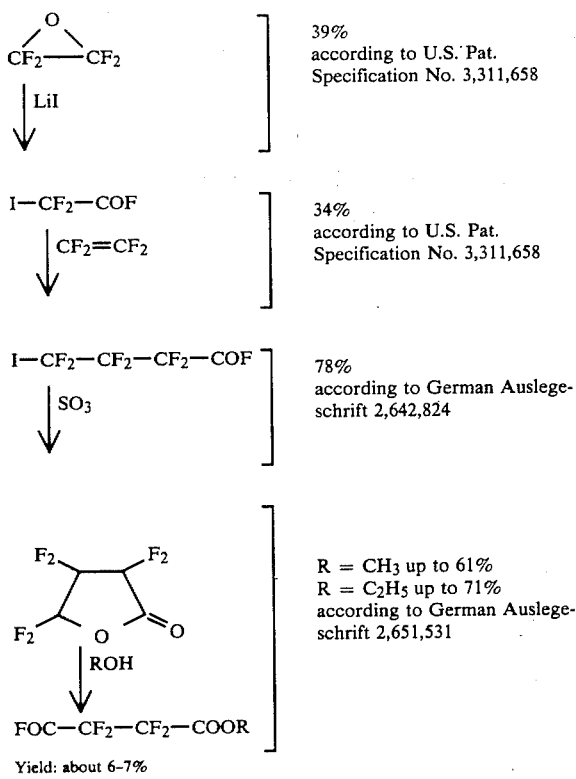

| | |
|---|---|
| | 39% according to U.S. Pat. Specification No. 3,311,658 |
| | 34% according to U.S. Pat. Specification No. 3,311,658 |
| | 78% according to German Auslegeschrift 2,642,824 |
| | R = CH₃ up to 61%<br>R = C₂H₅ up to 71%<br>according to German Auslegeschrift 2,651,531 |

Yield: about 6-7%

This route is far inferior to the route made possible by the invention because of its complexity and the poor yield.

The process according to the invention is itself distinguished by the fact that it is relatively simple to carry out and always gives high yields.

The invention thus represents a considerable advance in this field of the art.

The following examples are now intended to illustrate the invention further.

I.

PREPARATION OF COMPOUNDS OF THE FORMULA I IN WHICH A=HALOGEN

EXAMPLE 1

Preparation of fluorosulfato-difluoroacetyl fluoride (F—SO₂—O—CF₂—COF)

The electrolysis device comprises a cylindrical vessel which has an internal diameter of about 80 mm and is 250 mm in height and is provided with an external cooling jacket and a lid.

A dry ice condenser acting as a reflux condenser is mounted on the lid of the cell. The cell lid is also provided with further ground glass openings for insertion of a gas inlet tube, a thermometer and the current leads for the electrodes. The cylindrical anode of platinum gauze (diameter: 60 mm; height: 100 mm; mesh width: about 1 mm) is at a distance of about 20 mm from the bottom of the cell and is attached to the cell lid. A second cylinder of platinum gauze (diameter: 20 mm; height: 100 mm) forms the cathode, which is also held on the cell lid. A bar magnet encased in PTFE on the bottom of the cell is used as the stirrer. The cell is cooled by a cooling circulation with an inert coolant, for example perchloroethylene or trifluorotrichloroethane. All the components of the apparatus which come into contact with the medium are made of glass, platinum or PTFE. A solution of potassium fluorosulfonate in fluorosulfonic acid is used as the base electrolyte and is prepared as follows:

25 g (0.33 mole) of pure potassium chloride are initially introduded into the cell, and 500 g of distilled fluorosulfonic acid are slowly added, hydrogen chloride escaping, with vigorous foaming. A colorless solution is formed and is freed from residual hydrogen chloride by introduction of dry nitrogen and then pre-electrolyzed at a current strength of 8A for 3–5 hours.

250 g (2.55 moles) of gaseous difluoroacetyl fluoride (CHF₂COF) are passed into the base electrolyte obtained according to the above description at a current strength of 8A and at a temperature of 25°–30° C. in the course of 12 hours, with stirring. After a further 250 g of fluorosulfonic acid have been added, the electrolysis is continued for another 12 hours at a current strength of 8A, the cell voltage rising from an initial value of about 6 volts to about 12–15 volts.

Rectification of the electrolysis mixture over a 0.5 m packed column gives 438 g of product of boiling point 40°–42° C., which consists of about 13% by weight of fluorosulfonic acid and 87% by weight of fluorosulfatodifluoroacetyl fluoride.

¹⁹F—NMR (CDCl₃)* +50.04 (1F, —O—SO₂—F); +15.3 (1F, —CO—F); −77.2 (2F, —CF₂);

IR (gas spectrum): 5.25μ (C=O); 6.70μ (S=O).

*CFCl₃ is used as the internal standard for all the ¹⁹F-NMR spectra.

The yield, relative to the difluoroacetyl fluoride employed, is 77% of theory.

EXAMPLE 2

Preparation of 3-fluorosulfato-perfluoropropanoic acid fluoride (F—SO₂—O—CF₂—CF₂—COF)

Using an electrolysis cell and after preparation of a base electrolyte from 500 g of fluorosulfonic acid and 25 g of potassium chloride as described in Example 1, 395 g (2.67 moles) of 3-H-perfluoropropanoic acid fluoride (H—CF₂—CF₂—COF) are electrolyzed at a current strength of 8A and at a temperature of 20°–25° C. for 12 hours. Electrolysis is then continued for a further 24 hours at 5A, during which the cell voltage rises slowly from about 8 to 20 volts. The voltage can be reduced again to the initial value by briefly reversing the poles of the electrodes. When the electrolysis has ended, the charge which has passed is 216 Ah. Distillation of the electrolysis mixture up to a bottom temperature of 160° C. gives 585 g of distillate of boiling point 55°–78° C. Subsequent rectification over a 0.5 m packed column gives 120 g of a fraction of boiling point 53°–60° C., which consists of 70% by weight of 3-fluorosulfatoperfluoropropanoic acid fluoride and 30% by weight of fluorosulfonic acid. The following fraction of boiling point 60°–61° C. contains 420 g of approximately 98% pure fluorosulfatoperfluoropropanoic acid fluoride.

The yield is 74% of theory, relative to the starting material employed.

$^{19}F$—NMR (CDCl$_3$): +51.9 (1F, —O—SO$_2$F); +25.9 (1F, —CO—F); −84.8 (2F, —O—CF$_2$); −119.8 (2F, —CF$_2$).

IR (gas spectrum): 5.28μ (C=O), 6.67μ (S=O).

EXAMPLE 3

Preparation of 5-fluorosulfato-perfluoropentanoic acid fluoride (F—SO$_2$—O—CF$_2$—CF$_2$—CF$_2$—CF$_2$—COF)

Using an electrolysis cell and after preparation of a base electrolyte from 500 g of fluorosulfonic acid and 25 g of potassium chloride as described in Example 1, 410 g (1.65 moles) of 5-H-n-perfluoropentanoic acid fluoride (H—CF$_2$—CF$_2$—CF$_2$—CF$_2$—COF) are electrolyzed at a current strength of 8A for 8 hours and then, after addition of 120 g of fluorosulfonic acid, for a further 12 hours at 5A.

The electrolysis temperature is about 20°–25° C. 487 g of crude product are then separated off from the electrolysis mixture as a fluoro-organic phase by decanting, and a further 82 g of residual crude product of boiling point 56°–89° C. are driven off from the electrolyte phase by distillation up to a bottom temperature of 160° C. Rectification of the combined crude product on a 0.5 m packed column gives, in addition to 65 g of starting material, 344 g of product of boiling point 99°–101° C., which consists of 95% by weight of 5-fluorosulfatoperfluoropentanoic acid fluoride and 5% by weight of fluorosulfonic acid.

$^{19}F$—NMR (CDCl$_3$): +51.5 (1F, O—SO$_2$—F); +25.8 (1F, —COF); −82.9 (2F, —O—CF$_2$); −118.0 (2F, —CF$_2$); −122.3 (2F, —CF$_2$); −124.1 (2F, —CF$_2$—).

IR (gas spectrum): 5.3μ (C=O); 6.65μ (S=O).

The yield is 71% of theory, relative to the 5-H-n-perfluoropentanoic acid fluoride reacted.

EXAMPLE 4

Preparation of 5-fluorosulfato-perfluoropentanoic acid chloride (F—SO$_2$—O—CF$_2$—CF$_2$—CF$_2$—CF$_2$—COCl)

An electrolysis device equipped as described in Example 1 comprises a cylindrical glass vessel which has an internal diameter of 60 mm and is about 100 mm in height and has a cooling jacket, thermometer, gas inlet tube and dry ice condenser.

Instead of a platinum gauze, a plate (100×20×3 mm) of glassy carbon is used as the anode.

A 3 mm diameter rod of glassy carbon located at a distance of about 15 mm from the anode plate serves as the cathode.

The base electrolyte consists of a solution of potassium fluorosulfonate in fluorosulfonic acid, and is prepared by slowing adding 250 g of distilled fluorosulfonic acid to 12.5 g (0.165 mole) of pure potassium chloride and driving out the hydrogen chloride with a dry stream of nitrogen. The solution is then preelectrolyzed at a current strength of 2A.

After 117 g (0.44 mole) of 5-H-perfluoropentanoic acid chloride have been added, electrolysis is carried out at a current strength of 2A and at a temperature of 20°–25° C. until the charge which has passed reaches 44 Ah. The cell voltage is 15–19 volts.

When the electrolysis has ended, the fluoro-organic phase is separated off from the reaction mixture by decanting and subjected to fractional distillation on a 0.5 m packed column. 53 g (33% of theory) of 5-H-fluorosulfato-perfluoropentanoic acid chloride of boiling point 120°–121° C. are obtained.

$^{19}F$—NMR (CDCl$_3$): +52.0 (1F, O—SO$_2$—F); −82.4 (2F, —O—CF$_2$); −112.3 (2F, —CF$_2$—COCl); −120.7 (2F, —CF$_2$—); −123.3 (2F, —CF$_2$—).

EXAMPLE 5

Preparation of 8-fluorosulfato-perfluoro-2-methyl-3-oxaoctanoic acid fluoride (F—SO$_2$—O—(CF$_2$)$_5$—O—CF(CF$_3$)—COF)

Using an electrolysis device and after preparation of a base electrolyte from 250 g of fluorosulfonic acid and 12.5 g of potassium chloride as described in Example 4, 139.4 g (0.34 mole) of 8-H-perfluoro-2-methyl-3-oxaoctanoic acid fluoride (H—(CF$_2$)$_5$—O—CF(CF$_3$)COF) are electrolyzed at a current strength of 2A, a cell voltage of 12–13 V and a temperature of 20°–25° C. until the charge which has passed is 52 Ah.

182 g of fluoro-organic phase are separated off from the electrolysis mixture be decanting. Fractional distillation over a 0.5 m packed column gives 138.9 g (81% of theory) of 8-fluorosulfato-perfluoro-2-methyl-3-oxaoctanoic acid fluoride of boiling point 147°–148° C.

$^{19}F$—NMR (CDCl$_3$): +50.9 (1F, —O—SO$_2$—F); +26.6 (1F, —CO—F); −78.6 (1F, d, Jgem=150 Hz); −82.5 (3F, —CF$_3$); −83.6 (2F, —SO$_2$—O—CF$_2$—); −86.2 (1F, d, Jgem=150 Hz); −123.0 (2F, —CF$_2$—); −125.3 (2F, —CF$_2$—); −126.0 (2F, —CF$_2$—); −131.3 (1F, —CF—).

EXAMPLE 6

Preparation of 6-fluorosulfato-perfluoro-2-methyl-3-oxa hexanoic acid fluoride (F—SO$_2$—O—(CF$_2$)$_3$—O—CF(CF$_3$)—COF)

An electrolysis device as described in Example 4 is employed, but using cylindrical platinum electrodes (anode: diameter: 40 mm, height: 40 mm; cathode: diameter: 12 mm, height: 40 mm).

After preparation of a base electrolyte from 250 g of fluorosulfonic acid and 12.5 g of potassium chloride, 166 g (0.50 mol) of 6-H-perfluoro-2-methyl-3-oxa-hexanoic acid fluoride are electrolyzed at a current strength of 2A, a cell voltage of 5–6 V and a temperature of 20°–25° C. until the charge which has passed is 50 Ah. When the electrolysis has ended, the fluoro-organic layer is separated off by decanting and subjected to fractional distillation on a 0.5 m packed column. 146 g (68% of theory) of 6-fluorosulfato-perfluoro-2-methyl-3-oxa-hexanoic acid fluoride of boiling point 112°–114° C. are obtained.

$^{19}F$—NMR (CDCl$_3$): +50.6 (1F, —O—SO$_2$—F); +26.3 (1F, —CO—F); −78.2 (1F, d, Jgem=150 Hz); −81.8 (3F, —CF$_3$); −83.4 (2F, —SO$_2$—O—CF$_2$); −85.9 (1F, d, Jgem=150 Hz); −128.1 (2F, —CF$_2$—); −130.7 (1F, —CF—)

EXAMPLE 7

Preparation of 7-fluorosulfato-perfluoroheptanoic acid fluoride (FSO$_2$—O—(CF$_2$)$_6$—COF)

An electrolysis device as described in Example 4 is used. The base electrolyte consists of a solution of sodium fluorosulfonate in fluorosulfonic acid and is prepared by slowly adding 240 g of fluorosulfonic acid to 14.6 g (0.25 mole) of sodium chloride and driving out the hydrogen chloride with a dry stream of nitrogen. After preliminary electrolysis at a current strength of 2A for 5 hours, 43 g (0.124 mole) of 7-H-perfluoroheptanoic acid fluoride are added and electrolysis is carried out at a current strength of 2A and a cell voltage of 13–16 volts for 10 hours. The electrolysis temperature is 20° C. The electrolysis mixture is then subjected to fractional distillation over a 30 cm packed column. 16 g of a fraction which has a boiling point of 123°–158° C. and consists of two phases are thereby obtained. Redistillation of this fraction gives a fraction of boiling point 129°–131° C., which also gives two phases and is cooled to −18° C. in a separating funnel and separated into its phases. 35.5 g (64% of theory) of 7-fluorosulfato-perfluoroheptanoic acid fluoride are obtained as the lower phase.

$^{19}$F—NMR (CDCl$_3$): +50.87 (1F, OSO$_2$F); +25.28 (1F, —COF); −83.41 (2F, —CF$_2$—O—); −118.41 (2F, —CF$_2$—); −121.98 (2F, CF$_2$); −122.38 (2F, CF$_2$); −122.87 (2F, CF$_2$); −124.92 (2F, CF$_2$).

II

PREPARATION OF COMPOUNDS OF THE FORMULA I IN WHICH A=OR

EXAMPLE 8

Fluorosulfatodifluoroacetic acid methyl ester (FSO$_2$—O—CF$_2$—COOCH$_3$)

203 g of a mixture of 87% by weight of fluorosulfatodifluoroacetic acid fluoride ($\triangleq$0.9 mole) and 17% by weight of fluorosulfonic acid are dissolved in 200 ml of methylene chloride. The solution is cooled to +5° C. and a solution of 49 g (1.55 mole) of methanol in 62 ml of methylene chloride is then added dropwise. The internal temperature is kept below +10° C. by ice-cooling. The batch is subsequently stirred at room temperature for one hour. The reaction mixture is washed three times with 300 ml of water each time and dried over sodium sulfate. Distillation over a good column gives 153.5 g (82%) of the methyl ester with a boiling point of 119°–120° C.

Analysis: Calculated: C 17.31, H 1.45, F 27.39, S 15.41. Found: C 17.35, H 1.55, F 27.45, S 15.65.

$^1$H—NMR (CDCl$_3$): 4.02 (s)

$^{19}$F—NMR (CDCl$_3$): 49.9 (—O—SO$_2$F), −76.8 (CF$_2$)

IR (neat): 5.55μ (C=O), 6.75μ (S=O)

EXAMPLE 9

3-Fluorosulfatotetrafluoropropanoic acid methyl ester (FSO$_2$—O—CF$_2$—CF$_2$—COOCH$_3$)

A mixture of 29 g (0.9 mole) of methanol and 35 ml of methylene chloride is added dropwise to a solution, which has been cooled to 5° C., of 147.6 g (0.60 mole) of 3-fluorosulfatoperfluoropropanoic acid fluoride in 120 ml of methylene chloride such that the internal temperature does not rise above +10° C. During this addition, the batch is cooled with ice. It is subsequently stirred at room temperature for one hour. The reaction mixture is washed three times with 200 ml of water each time and dried over sodium sulfate. Distillation over a good column gives 133 g (86%) of the methyl ester with a boiling point of 75°–76° C. (100 mm).

Analysis: Calculated: C 18.61, H 1.17, F 36.80, S 12.42. Found: C 18.50, H 1.20, F 37.05, S 12.65.

$^1$H-NMR (CDCl$_3$): 4.03 (s)

$^{19}$F-NMR (CDCl$_3$): +50.7 (—OSO$_2$F), −85 (—O—CF$_2$), −120.1 (—CF$_2$—CO—)

IR (neat): 5.59μ (C=O), 6.72 (S=O)

EXAMPLE 10

3-Fluorosulfatotetrafluoropropanoic acid ethyl ester (FSO$_2$—O—CF$_2$—CF$_2$—COOC$_2$H$_5$)

Batch: 123 g (0.5 mole) of 3-fluorosulfatotetrafluoropropanoic acid fluoride, dissolved in 100 ml of methylene chloride 36.8 g (0.8 mole) of ethanol, dissolved in 40 ml of methylene chloride The reaction is carried out as described in Example 9 for the methyl ester. 109 g (77%) of the ethyl ester with a boiling point of 84° C. (100 mm) are obtained.

Analysis: Calculated: C 22.07, H 1.85, F 34.90, S 11.78. Found: C 22.00, H 1.80, F 34.80, S 11.90.

$^1$H-NMR (CDCl$_3$): 1.04 (t, J=7.2 Hz, 3H), 4.45 (q, J=7.2 Hz, 2H)

$^{19}$F-NMR (CDCl$_3$): +50.8 (—O—SO$_2$F), −84.5 (—O—CF$_2$), −119.9 (—CF$_2$—CO—)

IR (neat): 5.6μ (C=O), 6.73μ (S=O)

EXAMPLE 11

5-Fluorosulfato-octafluoropentanoic acid methyl ester (FSO$_2$—O—CF$_2$—CF$_2$—CF$_2$—COOCH$_3$)

A mixture of 26 g (0.81 mole) of methanol and 30 ml of methylene chloride is added dropwise to a solution of 150 g (0.43 mole) of 5-fluorosulfatoperfluoropentanoic acid fluoride in 100 ml of methylene chloride at 5° C. The batch has to be cooled with an ice-bath.

The batch is subsequently stirred at room temperature for one hour. The mixture is then washed three times with 200 ml of water each time and dried over sodium sulfate. Distillation over a good column gives 134 g (86%) of the methyl ester with a boiling point of 86°–87° C. (50 mm).

Analysis: Calculated: C 20.12, H 0.84, F 47.74, S 8.95. Found: C 20.05, H 0.80, F 47.35, S 9.25.

$^1$H-NMR (CDCl$_3$): 3.96 (s)

$^{19}$F-NMR (CDCl$_3$): +51.5 (—O—SO$_2$F), −82.6 (—O—CF$_2$), −118 (—CF$_2$—CO—), −122.4 (—CF$_2$—), −124 (—CF$_2$—)

IR (neat): 5.59μ (C=O), 6.69 (S=O)

EXAMPLE 12

5-Fluorosulfato-octafluoropentanoic acid methyl ester (FSO$_2$—O—CF$_2$—CF$_2$—CF$_2$-COOCH$_3$)

Batch: 36 g (0.1 mole) of 5-fluorosulfato-octafluoropentanoic acid chloride, dissolved in 30 ml of methylene chloride 4.8 g (0.15 mole) of methanol, dissolved in 10 ml of methylene chloride The reaction is carried out as described in Example 10. 30 g (84%) of the methyl ester are obtained.

EXAMPLE 13

7-Fluorosulfatoperfluoroheptanoic acid methyl ester (FSO$_2$—O—(CF$_2$)$_6$—COOCH$_3$)

A solution of 7.3 g (0.23 mole) of methanol in 30 ml of methylene chloride is added dropwise to a mixture of 40 g (0.089 mole) of 7-fluorosulfatoperfluoroheptanoic acid fluoride and 75 ml of methylene chloride, with ice-cooling. The internal temperature should not exceed +10° C. The batch is subsequently stirred at room temperature for 2 hours and is then washed several times with water and dried over sodium sulfate. Distillation over a packed column gives 29.6 g (72%) of 7-fluorosulfato-perfluoroheptanoic acid methyl ester with a boiling point of 96° C. (22 mm).

Analysis: Calculated: C 20.97, H 0.66, F 53.91, S 7.00. Found: C 20.7, H 0.6, F 54.0, S 6.7.

$^1$H-NMR (CDCl$_3$): 3.98 (s)

$^{19}$F-NMR (CDCl$_3$): +50.7 (1F, —OSO$_2$F), −83.23 (2F, —CF$_2$—O), −118.72 (2F, —CF$_2$—CO—), −122.34 (4F, 2× CF$_2$), −123.0 (2F, CF$_2$), −124.9 (2F, CF$_2$)

IR (neat): 5.59μ (CO), 6.70μ (SO)

EXAMPLE 14

5-Fluorosulfatoperfluoro-2-methyl-3-oxahexanoic acid methyl ester

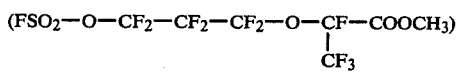
(FSO$_2$—O—CF$_2$—CF$_2$—CF$_2$—O—CF—COOCH$_3$)
                                         |
                                         CF$_3$ 22 g (0.053 mole) of 6-fluorosulfatoperfluoro-2-methyl-3-oxahexanoic acid fluoride and 30 ml of methylene chloride are cooled to about +5° C. A solution of 25 g (0.078 mole) of methanol in 30 ml of methylene chloride is added dropwise to the two-phase mixture, with cooling. During the reaction, the internal temperature is kept at 5°–10° C. The batch is stirred at room temperature for 2 hours and is then washed several times with water. The organic phase is dried over sodium sulfate and distilled. 18 g (80%) of the methyl ester with a boiling point of 158°–161° C. (760 mm Hg) are obtained.

Analysis: Calculated: C 19.82, H 0.71, F 49.27, S 7.56. Found: C 20.00, H 0.70, F 48.65, S 7.75.

$^1$H-NMR (CDCl$_3$): 3.97 (s)

$^{19}$F-NMR (CDCl$_3$): +51.34 (—OSO$_2$F), −78.2 (1F, —O—CF$_2$—, Jgem=150 Hz), −81.8 (CF$_3$), −83.1 (—CF$_2$—O—SO$_2$—), −85.4 (1F, —O—CF$_2$—, Jgem=150 Hz), −127.8 (CF$_2$), −131.3 (CF)

IR (neat): 5.6μ (C=O), 6.72μ (S=O)

EXAMPLE 15

8-Fluorosulfatoperfluoro-2-methyl-3-oxa-octanoic acid methyl ester

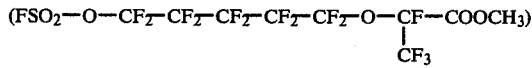
(FSO$_2$—O—CF$_2$—CF$_2$—CF$_2$—CF$_2$—CF$_2$—O—CF—COOCH$_3$)
                                                       |
                                                       CF$_3$ 126.5 g (0.25 mole of ω-fluorosulfatoperfluoro-2-methyl-2-oxa-octanoic acid fluoride and 100 ml of methylene chloride are cooled to about +5° C. A solution of 24 g (0.75 mole) of methanol in 30 ml of methylene chloride is added dropwise to the two-phase mixture, with good stirring. The internal temperature is kept at 5°–10° C. by cooling. The batch is subsequently stirred at room temperature for one hour and is then washed several times with water. The organic phase is dried over sodium sulfate and distilled. 102 g (79%) of the methyl ester with a boiling point of 80° C. (10 mm Hg) are obtained.

Analysis: Calculated: C 20.62, H 0.58, F 54.37, S 6.12. Found: C 20.55, H 0.55, F 54.15, S 6.30.

$^1$H-NMR (CDCl$_3$): 3.95 (s)

$^{19}$F-NMR (CDCl$_3$): +51.3 (—O—SO$_2$F), −78.1 (1F, —O—CF$_2$, Jgem=147 Hz), −82 (CF$_3$), −82.6 (—SO$_2$—O—CF$_2$), −85 (1F, —O—CF$_2$, Jgem=147 Hz), −122 (CF$_2$), −124.3 (CF$_2$), −125.1 (CF$_2$), −131.3 (CF)

IR (neat): 5.58μ (C=O), 6.7 (S=O)

We claim:

1. An ω-fluorosulfato-perfluorocarboxylic acid derivative of the formula

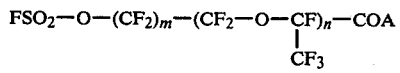
FSO$_2$—O—(CF$_2$)$_m$—(CF$_2$—O—CF)$_n$—COA
                                  |
                                  CF$_3$ in which A is halogen or OR wherein R is alkyl, m is a number from 1 to 10, and n is a number from 0 to 10.

2. The ω-fluorosulfato-perfluorocarboxylic acid derivative of claim 1 wherein A is chlorine.

3. The ω-fluorosulfato-perfluorocarboxylic acid derivative of claim 1 wherein A is fluorine.

4. The ω-fluorosulfato-perfluorocarboxylic acid derivative of claim 1 wherein R is alkyl having 1 to 10 carbon atoms.

5. The ω-fluorosulfato-perfluorocarboxylic acid derivative of claim 1 wherein R is CH$_3$.

6. The ω-fluorosulfato-perfluorocarboxylic acid derivative of claim 1 wherein R is C$_2$H$_5$.

7. The ω-fluorosulfato-perfluorocarboxylic acid derivative of claim 1 wherein m is a number from 1 to 8.

8. The ω-fluorosulfato-perfluorocarboxylic acid derivative of claim 1 wherein m is a number from 1 to 6.

9. The ω-fluorosulfato-perfluorocarboxylic acid derivative of claim 1 wherein n is a number from 0 to 4.

10. The ω-fluorosulfato-perfluorocarboxylic acid derivative of claim 3 wherein n is 0 or 1.

* * * * *